(12) United States Patent
Bengtson et al.

(10) Patent No.: US 7,699,831 B2
(45) Date of Patent: Apr. 20, 2010

(54) ASSEMBLIES, SYSTEMS, AND METHODS FOR VACUUM ASSISTED INTERNAL DRAINAGE DURING WOUND HEALING

(75) Inventors: Bradley P Bengtson, Grand Rapids, MI (US); Patricia A McGuire, Ladue, MO (US)

(73) Assignee: Surgical Design Solutions, LLC, Carson City, NV (US)

( * ) Notice: Subject to any disclaimer, the term of this patent is extended or adjusted under 35 U.S.C. 154(b) by 0 days.

(21) Appl. No.: 11/810,027

(22) Filed: Jun. 4, 2007

(65) Prior Publication Data

US 2007/0282310 A1    Dec. 6, 2007

Related U.S. Application Data

(63) Continuation-in-part of application No. 11/646,918, filed on Dec. 28, 2006.

(60) Provisional application No. 60/810,733, filed on Jun. 2, 2006.

(51) Int. Cl.
*A61M 1/00* (2006.01)
*A61M 27/00* (2006.01)

(52) U.S. Cl. ............... 604/541; 604/543; 604/540; 604/313

(58) Field of Classification Search .......... 602/2; 606/214; 604/540, 541, 28
See application file for complete search history.

(56) References Cited

U.S. PATENT DOCUMENTS

| | | | |
|---|---|---|---|
| 3,394,702 A | 7/1968 | Heimlich et al. | |
| 3,589,368 A | 6/1971 | Jackson | |
| 3,595,241 A | 7/1971 | Sheridan | |
| 3,935,863 A | 2/1976 | Kliger | |
| 3,957,054 A | 5/1976 | McFarlane | |
| 4,217,904 A | 8/1980 | Zahorsky | |
| 4,257,422 A | 3/1981 | Duncan | |
| 4,317,452 A | 3/1982 | Russo et al. | |
| 4,398,910 A | 8/1983 | Blake et al. | |
| 4,432,853 A | 2/1984 | Banks | |
| 4,445,897 A | 5/1984 | Ekbladh et al. | |
| 4,523,920 A | 6/1985 | Russo | |
| 4,533,356 A | 8/1985 | Bengmark et al. | |
| 4,553,966 A | 11/1985 | Korteweg | |
| 4,579,555 A | 4/1986 | Russo | |
| D288,962 S | 3/1987 | Blake | |
| 4,969,880 A | 11/1990 | Zamierowski | |

(Continued)

FOREIGN PATENT DOCUMENTS

WO    WO2004/041346 A1    5/2004

OTHER PUBLICATIONS

Product Brochure "Closed Systems for Management of Wound Drainage" Sterion Incorporated (Undated).

(Continued)

*Primary Examiner*—Tatyana Zalukaeva
*Assistant Examiner*—Susan Su
(74) *Attorney, Agent, or Firm*—Ryan Kromholz & Manion, S.C.

(57) ABSTRACT

Assemblies, systems, and methods convey fluid from an internal wound site or body cavity by applying negative pressure from a source outside the internal wound site or body cavity through a wound drain assembly that is placed directly inside the internal wound site or body cavity.

4 Claims, 7 Drawing Sheets

U.S. PATENT DOCUMENTS

| | | | |
|---|---|---|---|
| 5,045,075 | A | 9/1991 | Ersek |
| 5,053,021 | A | 10/1991 | Feibus |
| 5,085,633 | A | 2/1992 | Hanifl et al. |
| 5,100,395 | A | 3/1992 | Rosenberg |
| 5,116,310 | A | 5/1992 | Seder et al. |
| 5,180,375 | A | 1/1993 | Feibus |
| 5,358,492 | A | 10/1994 | Feibus |
| 5,360,414 | A | 11/1994 | Yarger |
| 5,437,651 | A | 8/1995 | Todd et al. |
| 5,451,204 | A | 9/1995 | Yoon |
| 5,549,579 | A | 8/1996 | Batdorf et al. |
| 5,554,138 | A | 9/1996 | Stanford et al. |
| 5,599,330 | A | 2/1997 | Rainin |
| 5,628,735 | A | 5/1997 | Skow |
| 5,636,643 | A | 6/1997 | Argenta et al. |
| 5,645,081 | A | 7/1997 | Argenta et al. |
| 5,678,564 | A | 10/1997 | Lawrence et al. |
| 5,911,222 | A | 6/1999 | Lawrence et al. |
| 5,921,972 | A | 7/1999 | Skow |
| 6,099,513 | A | 8/2000 | Spehalski |
| 6,235,009 | B1 | 5/2001 | Skow |
| 6,290,685 | B1 | 9/2001 | Insley et al. |
| 6,478,789 | B1 | 11/2002 | Spehalski et al. |
| 6,565,544 | B1 | 5/2003 | Rainin |
| 6,605,068 | B2 | 8/2003 | Righetti |
| 6,695,823 | B1 | 2/2004 | Lina et al. |
| 6,866,657 | B2 | 3/2005 | Shchervinsky |
| 6,979,324 | B2 | 12/2005 | Bybordi et al. |
| 7,004,915 | B2 | 2/2006 | Boynton et al. |
| 7,182,758 | B2 | 2/2007 | McCraw |
| 7,322,971 | B2 | 1/2008 | Shehada |
| 7,413,571 | B2* | 8/2008 | Zamierowski ............. 606/215 |
| 2001/0043943 | A1 | 11/2001 | Coffey |
| 2002/0128578 | A1 | 9/2002 | Johnston et al. |
| 2003/0109855 | A1 | 6/2003 | Solem et al. |
| 2004/0260230 | A1 | 12/2004 | Randolph |
| 2005/0004536 | A1 | 1/2005 | Opie et al. |
| 2005/0137539 | A1 | 6/2005 | Biggie et al. |
| 2006/0015087 | A1* | 1/2006 | Risk et al. ................ 604/541 |
| 2007/0027414 | A1* | 2/2007 | Hoffman et al. ............. 602/2 |

OTHER PUBLICATIONS

Product Brochure "BLUNT Seroma CATH® Wound Drainage System" Greer Medical, Inc. (Undated).

Product Brochure "Seroma Cath® Wound DrainageSystem" Greer Medical, Aug. 2002.

Product Brochure, V.A.C.® Therapy™ Dressings, Canisters and Accessories, KCI 2005.

Product Brochure, "An Insight into V.A.C.® Dressings", KCI 2005.

Saxena et al., "Vacuum-Assisted Closure: Microdeformations of Wounds and Cell Proliferation", Plastic and Reconstructive Surgery,JVol. 115, No. 5, pp. 1086-1096, Oct. 2004.

Cholmondeley Williams, et al.,"The Effect of Hematoma on the Thickness of Pseudosheaths Around Silicone Implants", presented at the Am Soc of Plastic and Reconstructive Surgeons, Houston, TX, Oct. 30, 1974.

Shermak, Michele A. et al., "Seroma Development Following Body Contouring Surgery for Massive Weight Loss: PatietnRisk Factors and Treatment Strategies", Division of Plastic Surgery and the Department of Surgery, the Johns Hopkins Medical Institutions, pp. 28088; Jul. 12, 2007.

Product description Endo Sponge, www.bbraun.com, Jun. 18, 2008.

Mees, et al., "Endo-vacuum Assisted Closure Treatment for Rectal Anastomotic Insufficiency" Diseases of Colon and Rectum, vol. 51: 404-410, 2008.

* cited by examiner

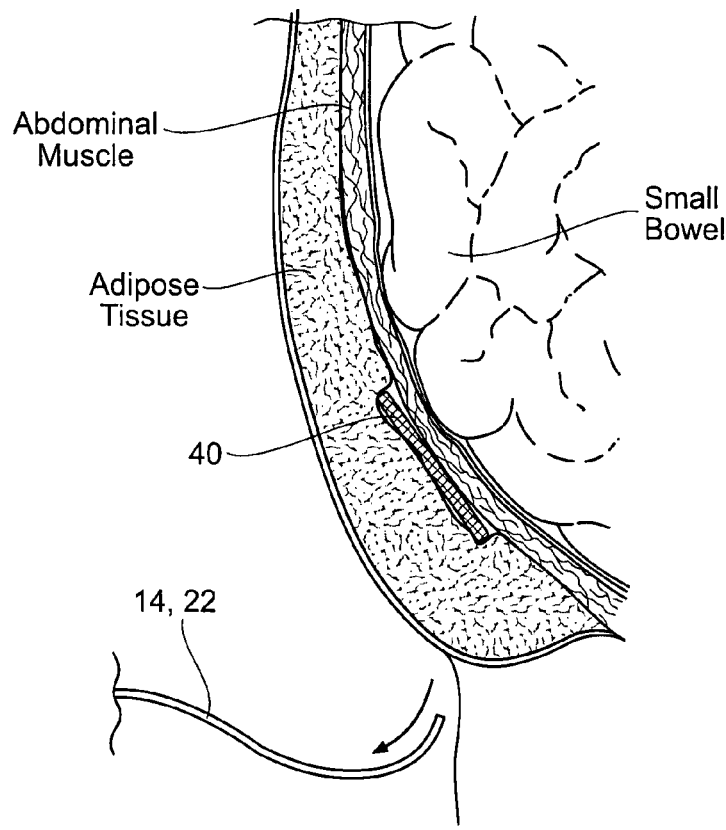
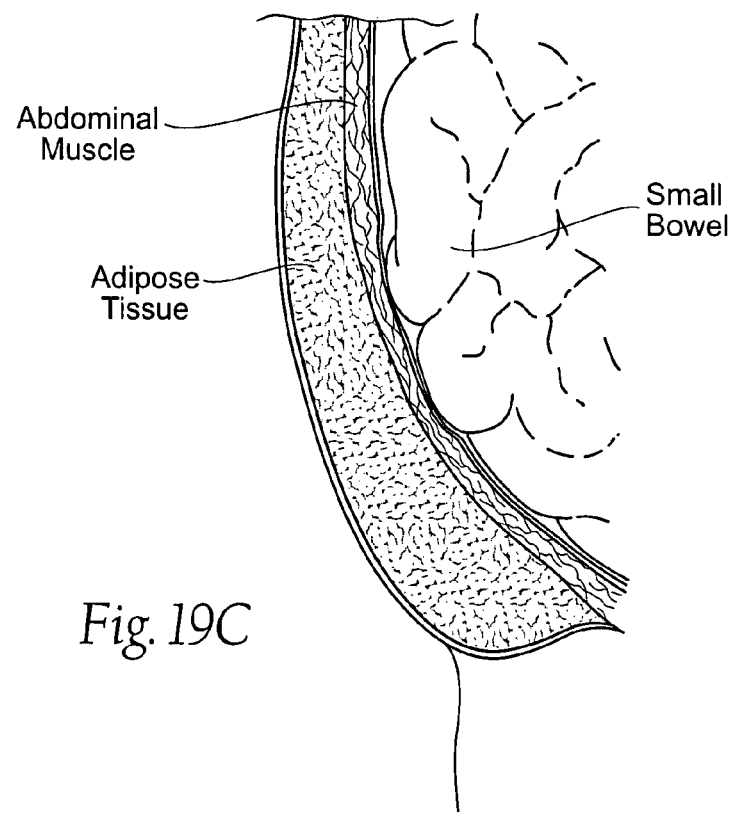

ASSEMBLIES, SYSTEMS, AND METHODS FOR VACUUM ASSISTED INTERNAL DRAINAGE DURING WOUND HEALING

RELATED APPLICATION

This application is a continuation-in-part of co-pending U.S. patent application Ser. No. 11/646,918, filed Dec. 28, 2006 and entitled Assemblies, Systems, and Methods for Vacuum Assisted Internal Drainage During Wound Healing, which claims the benefit of U.S. Provisional Patent Application Ser. No. 60/810,733, filed Jun. 2, 2006, and entitled "Foam Sponge Vacuum Assisted Internal Drainage System," which are each incorporated herein by reference.

FIELD OF THE INVENTION

This application relates generally to the drainage of fluid from the body during the wound healing process, e.g., following surgery, trauma, or placement of implants or surgical devices.

BACKGROUND OF THE INVENTION

During surgery, or as a result of trauma, tissue volume can be removed or altered, and an open or dead space is created within the tissue that was previously attached to other tissue. The very small blood vessels that previously ran from the underlying tissue (i.e., muscle, connective tissue) to the overlying tissue (i.e., skin, muscle) can be cut or damaged. Although these vessels usually do not cause significant blood loss, they do allow escape of blood serum into the area. Human blood serum contains about ninety-three percent water and about seven percent protein (mostly albumin).

Following surgery or due to trauma, there can also be resulting tissue damage, regardless of how careful the surgeon is. This tissue damage results in cellular death, and the body's natural defense reaction is an inflammatory one. Because of the inflammation, cell death, and increased vascular permeability, fluid can also accumulate in the operative space. The larger the operative space, the greater is the potential for internal fluid collection.

The body can resolve the accumulation of fluid over time, if there is some form of natural drainage, and if there is not continued irritation to the area, and if circulation to the area is sufficient, and if the person is in good health or the volume of fluid collection is itself not too large.

If, for whatever reason, the body is unable to itself efficiently absorb the excess fluid, a seroma can occur. A seroma is defined as a sterile accumulation of blood serum in a circumscribed tissue location or operative space. A seroma is not by definition an "infection;" it does not necessarily involve the presence of white blood cells, bacteria, and the breakdown products of both. A seroma is fluid and blood serum that has accumulated in a dead space in the tissue. A seroma is the result of tissue insult and the product of tissue inflammation and the body's defense mechanisms.

Seromas commonly develop following drain removal or when fluid is produced at a greater rate than it is absorbed. Conventional wound management techniques are commonly applied when a seroma becomes a clinical concern. Placement of a seroma catheter or additional drain, as well as repeated or serial drainage of a seroma, may be required. A seroma or fluid collection is by far the most common complication in surgery today. Such complications result in a significant amount of lost income to patients, as well as expenses to insurers and physicians who have to care for these patients that require serial drainage. Such complications also delay wound healing, may entail additional surgical procedures, and ultimately delay the patient's return to work and routine functional activity. Seroma management can also be costly and, further, can place health care workers to additional needle exposure risks and related outcomes such as hepatitis, etc.

The aim of wound management in both chronic and acute situations is to assist the natural process and prevent further complications such as infection, slough, necrosis formation, and chronic seroma cavities. Maintenance of the optimum wound healing environment is essential, ensuring the wound is kept moist and warm. Wound care products strive to achieve these results and, in turn, help to promote rapid wound closure.

Fluid drainage can be as simple as creating an opening at the lowest edge of the seroma, and keeping this open and clean to allow continued drainage. A clinically accepted way to deal with a seroma that does not appear to be resolving on its own, is to install a continuous drain system, coupled with treatment with antibiotics to prevent infection while the continuous drain system is in use. There are currently numerous types of wound drains on the market, most of them utilizing some form of tubing to withdraw fluid from the wound until the body can resorb the fluid without assistance. A continuous drain system allows the fluid to continuously escape until the body can complete the healing process on its own.

A representative prior art continuous drain system can comprise an implanted device such as a piece of rubber tubing (Penrose drain) (as shown in FIG. 1), which provides dependent gravity drainage or responds to a negative suction force generated by a manual closed suction bulb. These types of drains constitute the most common devices currently available. The problem with these devices is that, although they may drain fluid, fluid drainage is limited to fluid directly around the drain itself. As a result, current drains may manage fluid collection, but they do not effectively clear all of the fluid in the space and, more importantly, they do not clear enough fluid to effectively seal down and close off the dead space.

Another representative prior art continuous drain system, which is currently approved for external use only, can take the form of an externally applied device comprising a piece of foam with an open-cell structure, which coupled to one end of a drain tube (see FIG. 2). The foam is placed externally on top of the wound or skin, and the entire external area is then covered with a transparent adhesive membrane, which is firmly secured to the healthy skin around the wound margin. The opposite end of the drain tube is connected to a vacuum source, and blood or serous fluid are drawn from the wound through the foam into a reservoir for subsequent disposal. Among the numerous names this prior art system is called are "Vacuum Assisted Closure device" or VAC devices. Conventional VAC devices, however, are only approved and used for external wounds only. Conventional VAC devices are not approved or used for internal wounds or operative sites.

Current wound drain devices assemblies at times do not remove a substantial amount of fluid from within a wound and have other performance issues. For example, external VAC devices clear fluid directly around external wounds (as FIG. 3 shows), and they are limited to the application to external wounds only. They leave the remainder of the wound site or operating space open and filled with fluid.

Furthermore, the clinical use of external VAC devices may not make wound drainage more cost-effective, clinician-friendly, and patient-friendly.

For example, the foam structures and adhesive membranes associated with conventional practices of external VAC need to be periodically removed and replaced. Currently, dressing changes are recommended every 48 hours for adults with non-infected wounds, and daily for infants and adolescents. Current techniques place the foam material in direct contact with granulating tissue. Removal of the foam structures in the presence of granulating tissue and the force of pressure on the wound bed that this removal can cause pain or discomfort. The sponge can also de-particulate and remain in the wound. Furthermore, the multiple steps of the conventional external VAC procedure—removing the adhesive membrane, then removing the old foam structures, then inserting the new foam structures, and then reapplying the adhesive member along the entire periphery of the wound—are exacting, tedious and time consuming. They only prolong pain or discomfort, and cause further disruption to the patient, and also demand dedicated nursing time and resources.

Furthermore, to function correctly, the adhesive membrane applied over the foam wound structures must form an airtight seal with the skin. Obtaining such a seal can be difficult, particularly in body regions where the surrounding skin is tortuous, and/or mucosal and/or moist.

Furthermore, prolonged wearing of wet dressings can cause further breakdown and maceration of the surrounding skin thereby increasing the wound size. This can cause further discomfort to the patient, and the exudate can often be offensive in odor and color causing further embarrassment to the patient. This may, in turn, require more numerous dressing changes and re-padding throughout the day, which is disruptive to the patient and costly both in terms of nursing time and resources.

Furthermore, since the membrane and the material of the foam structures are both in direct contact with tissue, tissue reactions can occur.

There remains a need for improved drains, systems, devices, methods that are cost-effective, patient-friendly, and clinician-friendly.

SUMMARY OF THE INVENTION

The invention provides assemblies, systems, and methods that are cost-effective, patient-friendly, and clinician-friendly. The assemblies, systems, and methods convey fluid from an internal wound site or body cavity by applying negative pressure from a source that is outside the internal wound site or body cavity through a wound drain assembly that is placed directly inside the internal wound site or body cavity. Unlike conventional VAC devices, the assemblies, systems, and methods that embody the technical features of the invention are not a treatment modality that is limited to placement on an exterior wound or operational site following trauma or surgery, providing drainage in a reactive and localized fashion. Instead, the assemblies, systems, and methods that embody the technical features of the invention make possible a treatment modality that is sized and configured for placement directly inside an internal wound site or body cavity at the time of surgery, to provide direct and immediate drainage of any entire wound site in a proactive fashion.

One aspect of the invention provides a wound drain assembly comprising a housing enclosing an open interior. The housing is sized and configured for placement directly within an interior wound site or body cavity. Perforations in the housing communicate with the open interior. A foam sponge material is carried within the open interior. The foam sponge material absorbs fluid residing in the interior wound site or body cavity. Tubing is coupled to the housing in communication with the open interior of the housing. The tubing extends from within the interior wound site to outside the interior wound site or body cavity. The tubing outside the interior wound site or body cavity is sized and configured to be coupled to a source of negative pressure outside the body cavity. The negative pressure conveys through the tubing fluid that is absorbed by the foam sponge material inside the internal wound site or body cavity.

Another aspect of the invention provides a wound drain system comprising a wound drain assembly as just described, which is coupled to a source of negative pressure outside the body cavity.

Another aspect of the invention provides a wound drain assembly comprising a wound drainage structure comprising a material capable of being absorbed by the body. The wound drainage structure is sized and configured to absorb fluid in an interior wound site or body cavity. According to this aspect of the invention, tubing is releasably coupled to the wound drainage structure. The tubing extends outside the interior wound site or body cavity to be coupled to a source of negative pressure outside the body cavity to convey fluid absorbed by the material from the internal wound site or body cavity. After conveying the desired volume of fluid from the body, the tubing can be disconnected from the wound drainage structure, to allow the wound drainage structure to be absorbed by the body.

Other aspects of the invention provide methods that provide the wound drain assembly or system as above described and that operate the assembly or system to convey fluid from an interior wound site or body cavity.

The assembly, system, and/or method apply a vacuum of significant pressure internally and directly in a wound area or body cavity for enhanced wound healing benefits. By applying a vacuum of significant consistent pressure internally and directly in the wound area or body cavity, the assembly, system, and/or method reduce the "dead-space" or open area inside the wound or cavity, and thereby aid in decreasing tissue edema and swelling of the overlying and underlying tissue. The assembly, system, and/or method increase the nature and extent of wound drainage, promote tissue adherence and closure of wounds, and thus decrease seroma formation and promote primary wound healing. The assembly, system, and/or method thereby decrease the costly and increased patient morbidity caused by seroma formation and the resultant delay in primary wound healing or need for additional surgical procedures or drainage.

BRIEF DESCRIPTION OF THE DRAWINGS

FIGS. 19A, 19B, and 19C show, in an anatomic view, s system like that shown in FIG. 4, comprising an absorbable would drain assembly.

DESCRIPTION OF THE PREFERRED EMBODIMENT

Although the disclosure hereof is detailed and exact to enable those skilled in the art to practice the invention, the physical embodiments herein disclosed merely exemplify the invention that may be embodied in other specific structure. While the preferred embodiment has been described, the details may be changed without departing from the invention, which is defined by the claims.

Figure 1:
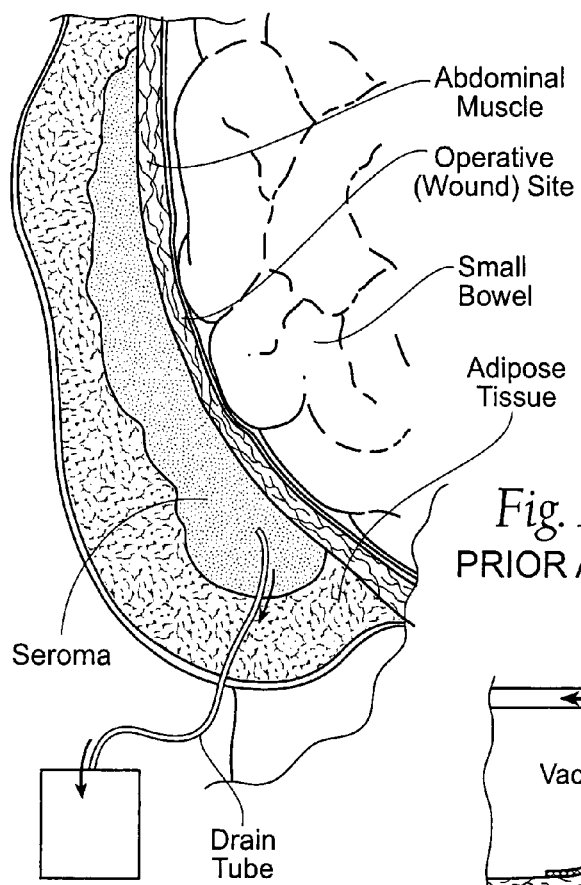
FIG. 1 is an anatomic side section prior art view of a human abdomen showing an interior wound area and a tube that is placed according to conventional techniques to drain fluid from a seroma at the wound site.
Figure 2:
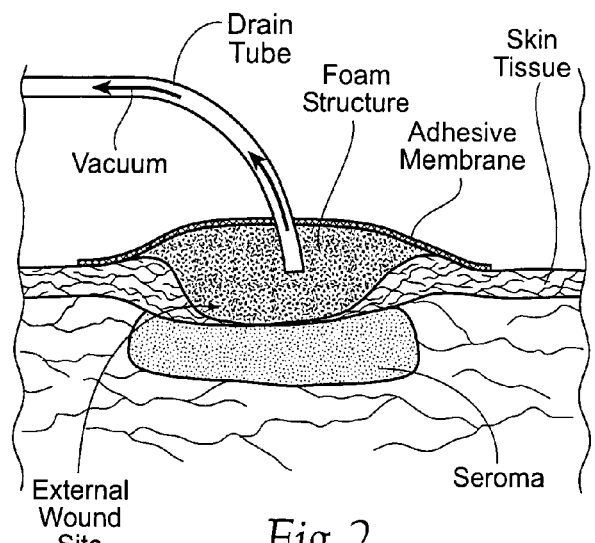
FIG. 2 is an anatomic side section prior art view of an exterior wound area showing an external VAC device placed according to conventional techniques to drain fluid from a seroma only at an external wound site.
Figure 3:
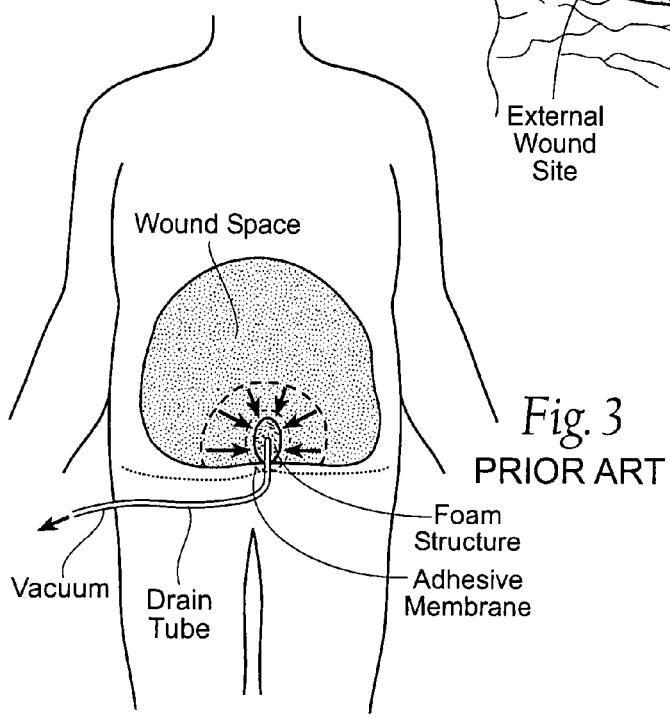
FIG. 3 is an anatomic, somewhat diagrammatic prior art view of the limited drainage area achieved by the external VAC device shown in FIG. 2.
Figure 4:
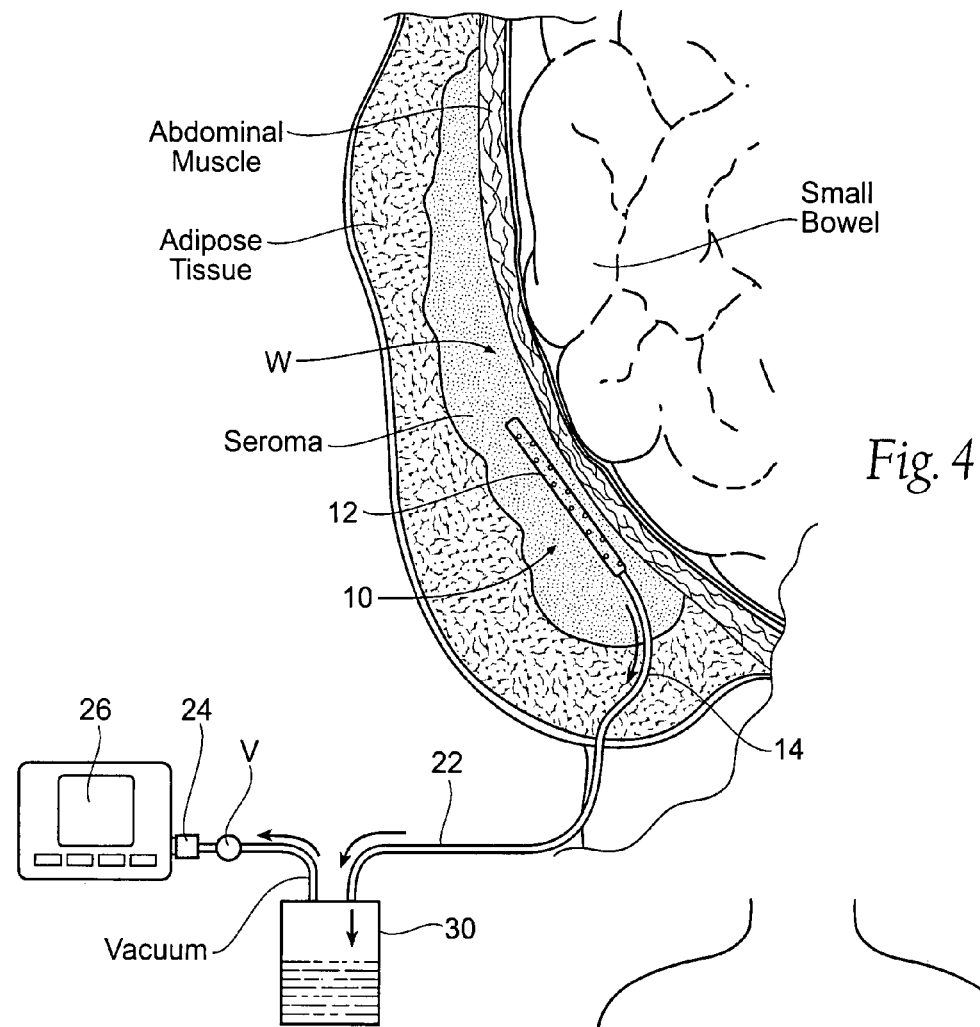
FIG. 4 is an anatomic side section view of a human abdomen, like that shown in FIG. 1, but showing a drain system that embodies features of the invention, comprising an internally placed wound drain assembly coupled to an external source of negative pressure.

FIG. 4 shows a wound drainage system 10 comprising an internal drain assembly 12 that is sized and configured for surgical placement within a wound area W (or body cavity). The wound area W may be anywhere in a human or animal, e.g., within a body cavity, or beneath the skin, or in muscle, or within the soft tissues. As will be described in greater detail later (see FIG. 6), the internal drain assembly 12 includes a housing 18 that encloses a foam sponge component 16. The foam sponge component 16 communicates with the wound area W through one or more apertures 20 formed in the housing 18.

The internal drain assembly 12 is coupled to drain tubing 14, which is desirable flexible. The drain tubing 14 extends outside the wound area W. The drain tubing 14 can extend through a percutaneous incision in the skin overlying any wound area W. Alternatively, the drain tubing 14 can extend through an opening in a skin flap bounding the wound area. The flexible drain tubing 14 includes a terminal end 22 that extends outside the body.

The terminal end 22 desirably includes a quick release connector 24. The connector 24 is sized and configured to be connected to a conventional external negative pressure suction device 26 (such as a V.A.C.® device made by KCI International, or a conventional wall suction or other regulated vacuum device).

In use, the drain tubing 14 is connected to the suction device 26, and the suction device 26 is operated to apply a requisite negative pressure through the internal drain assembly 12. Blood or serous fluid absorbed by and passing through the foam sponge component 16 are drawn by the negative pressure from the wound area W. The drain tubing 14 desirably includes an inline reservoir 30 to collect the withdrawn fluid for disposal.

Figure 5:
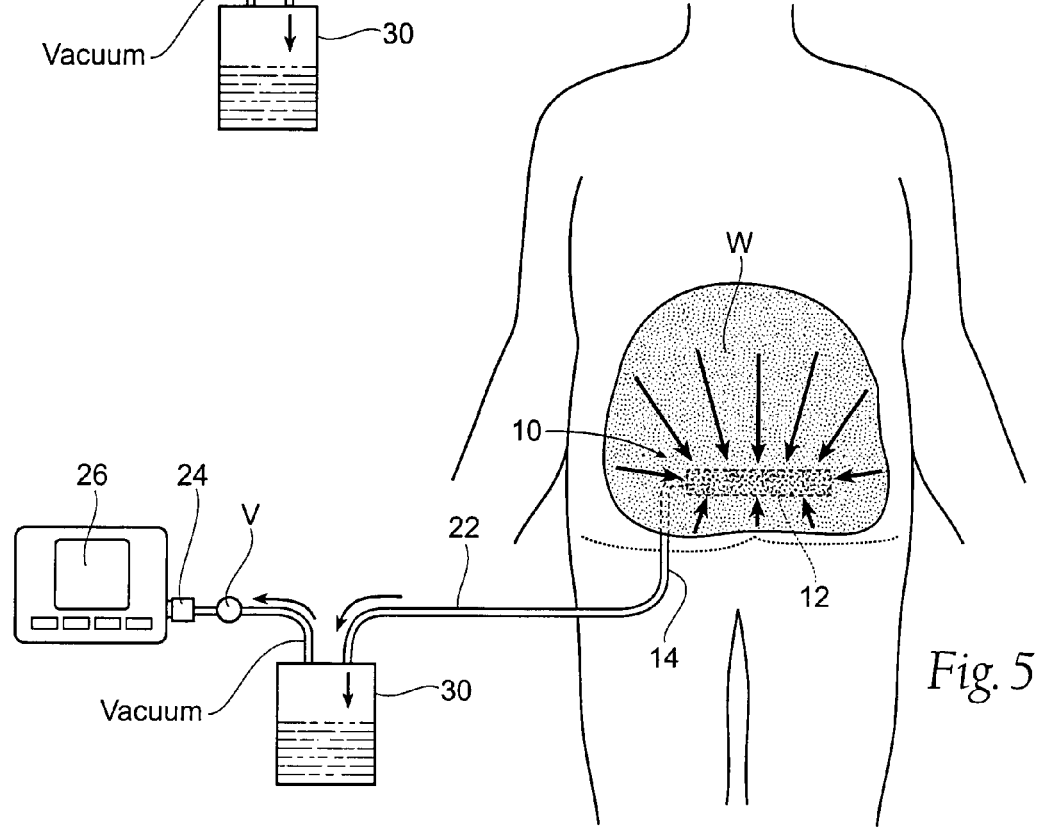
FIG. 5 is an anatomic, somewhat diagrammatic view of the enhanced drainage area achieved by the drain system shown in FIG. 4.

As FIG. 5 shows, occupying the interior of the wound area W, the internal drain assembly 12 conveys negative pressure throughout the entire open volume of the wound space. The negative pressure applied by the internal drain assembly 12 clears fluid from the entire wound volume. The removal of fluid from the entire wound volume promotes tissue adherence within the wound space, to close the wound space and seal the wound.

As FIGS. 4 and 5 show, the drain tubing 14 desirably includes an inline one-way backflow valve V. The one-way backflow valve V allows fluid to be drawn from the wound volume into the reservoir 30. Upon disconnection of the drain tubing 14 from the external negative pressure suction device 26 (via the connector 24), the one-way backflow valve V prevents air or fluid to flow backward into the wound or body. The one-way backflow valve V keeps the internal drain assembly 12 closed when not connected to the external negative pressure suction device 26.

Figure 6:
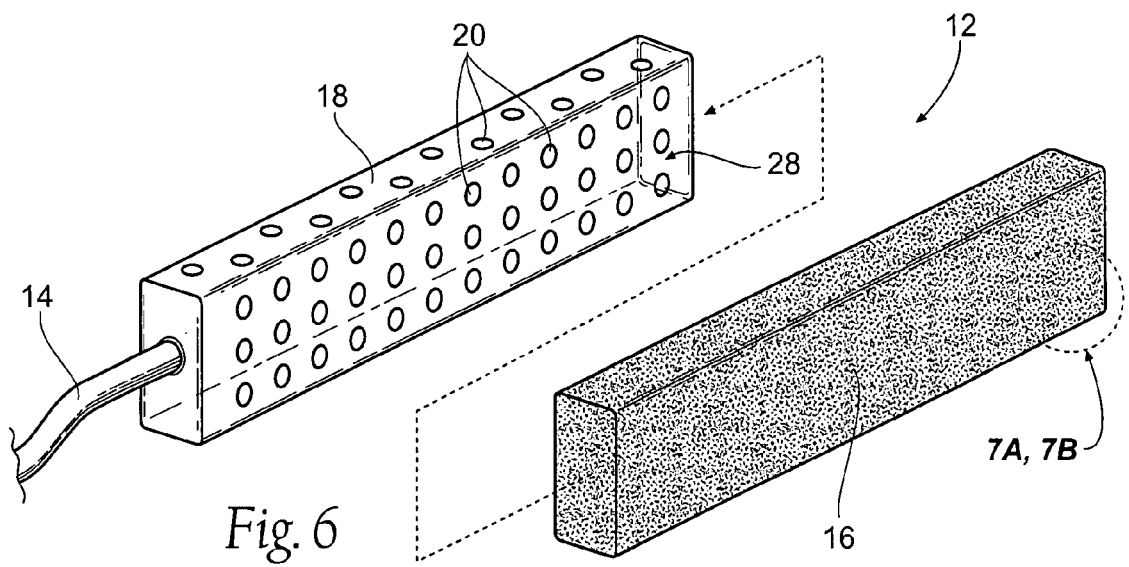
FIG. 6 is a perspective, exploded view of a representative embodiment of a wound drain assembly of the type shown in FIG. 4.
Figure 8:
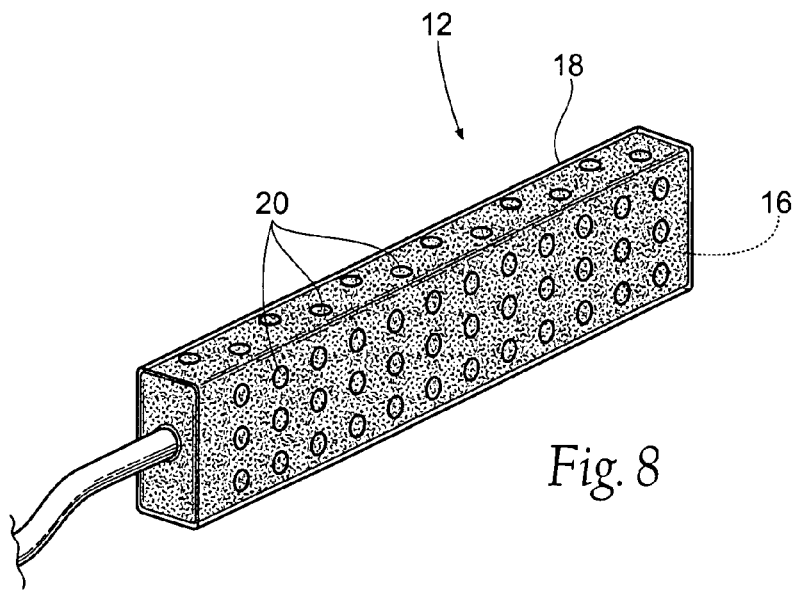
FIG. 8 is a perspective, assembled view of the wound drain assembly shown in FIG. 6.
Figure 9:
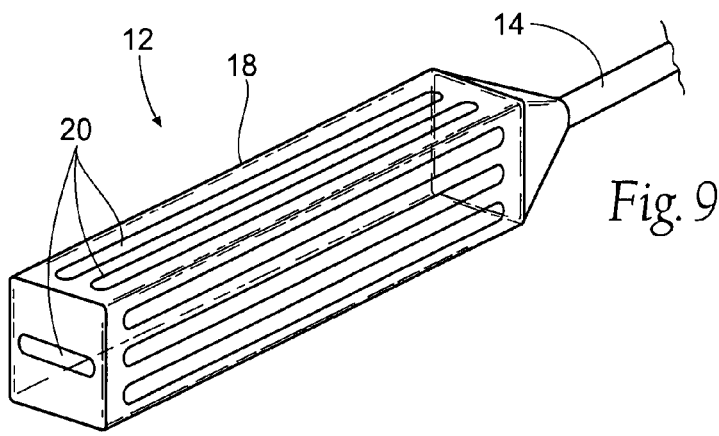
FIGS. 9 to 13 are perspective views of other representative embodiments of a wound drain assembly of the type shown in FIG. 4.
Figure 10:
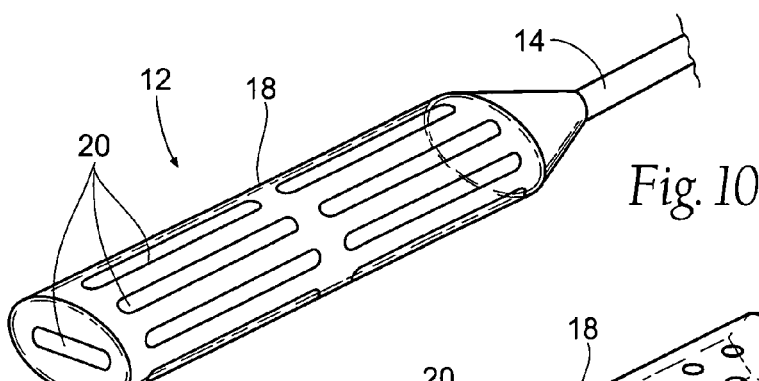
Figure 11:
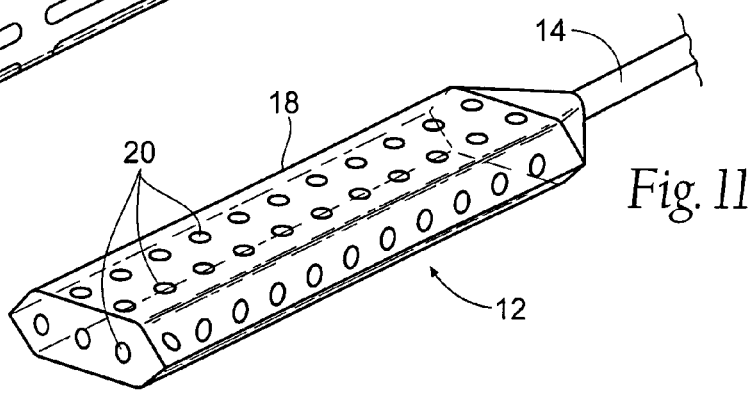
Figure 12:
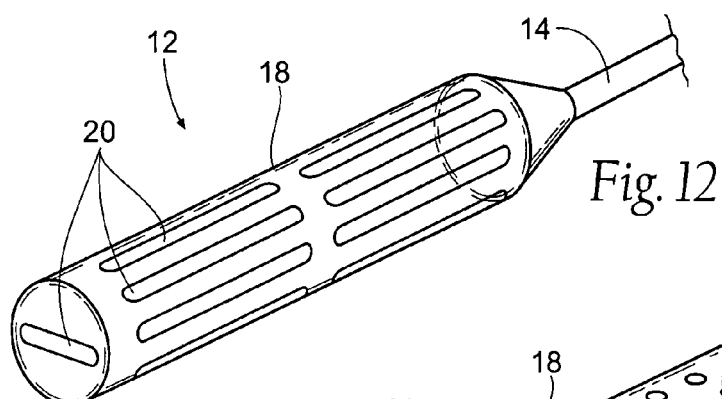
Figure 13:
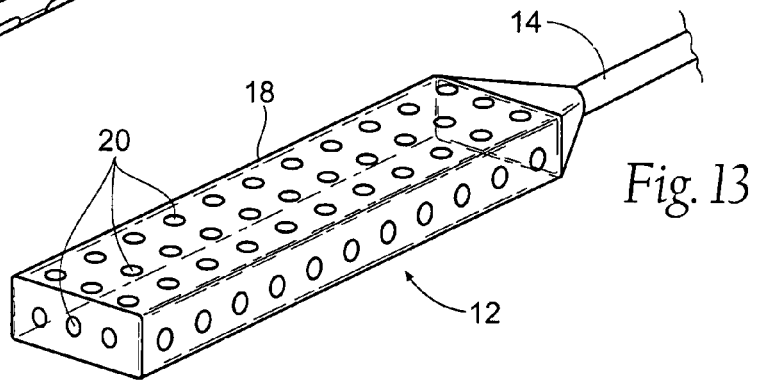

As FIGS. 6 and 8 show, the internal drain assembly 12 comprises a housing 18. The housing 18 is made from an inert, biocompatible material that does not adhere to or activate the body's natural foreign body defense mechanism. The material can comprise, e.g., silicone rubber, polyurethane, or other biocompatible plastics.

The housing 18 can be formed. e.g., by extrusion, molding, or machining. As will be described in greater detail later, the housing 18 can be formed in various shapes and sizes, depending upon the requirements and morphology of the wound site and function and use of the drain. In the configuration shown in FIG. 8, a representative size measures about 5" (length)×about ¾" (width)×about ½" (height).

The housing 18 is formed to include a hollow interior chamber 28, which is enclosed by the side and end walls of the housing 18. The housing 18 is also formed to include one or more through-slots, through-apertures, or through-perforations 20 in the side and/or end walls of the housing 18. The through-slots, through-holes, or through-perforations 20 open the hollow interior chamber 28 to communication with the wound site environment outside the housing 18.

An end of the flexible drain tubing 14 is coupled to the housing 18 and opens into the hollow interior chamber 28. The flexible drain tubing 14 is made of medical grade, inert material, e.g., silicone rubber, polyurethane, or other biocompatible plastics. The tubing 14 is desirably sized and configured to accommodate sufficient fluid flow with a relatively small and tolerable incision size (e.g., about 2-3" in diameter).

Figure 7A:
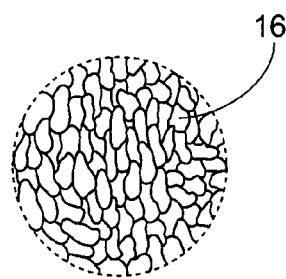
FIGS. 7A and 7B are enlarged views of representative forms of foam sponge material that the wound drain assembly shown in FIG. 6 carries.
Figure 7B:
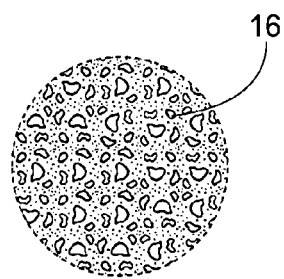

A foam sponge component 16 is housed within the hollow interior chamber 28. The foam sponge component 16 is characterized in that it does not particulate in the presence of fluid and pressure. The foam sponge material can comprise, e.g., an open-cell porous structure (see FIG. 7A) or a granulated foam construction (see FIG. 7B). The foam sponge component 16 can be variously constructed from a biocompatible material that does not adhere to or activate the body's natural foreign body defense mechanism, e.g., sponge materials used with conventional VAC devices. As stated later, the foam sponge component 16 can be impregnated with antibacterial products or solutions, or other hormone or natural or man-made stimulating factors that can decrease the chance of infection and/or accelerate wound healing.

In use (as FIGS. 4 and 5 show), the internal drain assembly 12 is placed within an interior of the wound area W (or body cavity). Fluids collecting in the wound or body cavity are absorbed by and pass through the foam sponge component 16 through the perforations 20 in the housing 18. Fluid absorbed by the foam sponge component 16 is siphoned away by the drain tubing 14 when a requisite negative pressure is applied.

The negative pressure can be, e.g., 125 to 200 mmHg, and is desirably about 125 mmHg, below ambient pressure. The amount of negative vacuum pressure can be regulated in a continuous, discontinuous, or otherwise variable manner, to maximize wound healing and closure and thereby reduce overlying soft tissue edema and swelling. In this way, the system 10 promotes primary wound healing while also decreasing or minimizing seroma formation.

Figure 16:
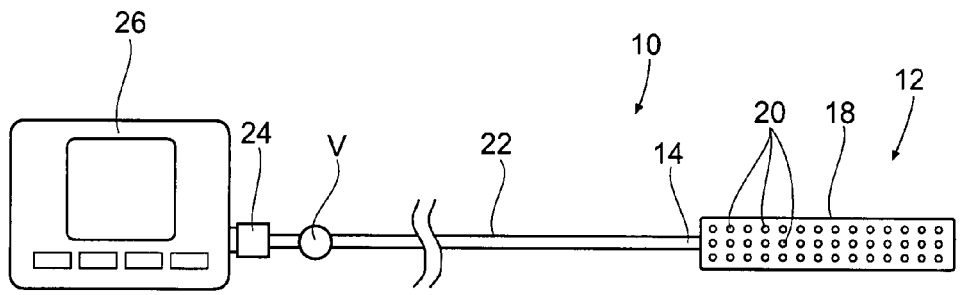
FIGS. 16 and 17 show, respectively, a wound drain assembly of the type shown in FIG. 4 before and during the application of negative pressure.
Figure 17:
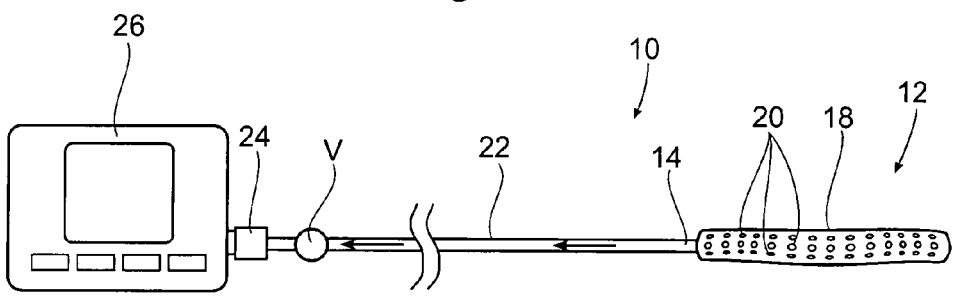

As FIGS. 16 and 17 show, the introduction of negative pressure into the housing 18 can cause the housing 18 to collapse against the foam sponge component 16 (as FIG. 17 shows), while the through-perforations 20 of the housing 18 maintain open paths for fluid to be absorbed by the foam sponge component 16.

The foam sponge component 16 is desirably compressible for easy insertion into and removal from the housing 18 for replacement. The configuration of the housing 18 can also provide a contour that facilitates sliding of the internal drain assembly 12, easing removal from the body.

The foam sponge component 16 may also be impregnated with components such as silver or antibacterials or other growth factors that may decrease infection and promote wound healing. The foam sponge component may also include other hormone or natural or manmade stimulating factors that can decrease the chance of infection and/or accelerate wound healing.

As FIGS. 9 to 13 show, the housing 18 can be formed in various dimensions, shapes, and sizes, and the foam sponge component 16 cut to corresponding dimensions, shapes, and sizes. These dimensions, shapes, and sizes can comprise, e.g., square (FIG. 9); oval (FIG. 10); hexagonal (FIG. 11); round (FIG. 12); or rectangular (FIG. 13); or any linear or curvilinear shape or combinations thereof. The ends of the housing 18 can be tapered or not tapered (as FIGS. 9 to 13 demonstrate) The through-perforations 20 can also be variously shaped and sized (as FIGS. 9 to 13 demonstrate). The through-perforations 20 can also be tapered or not tapered along their axes.

Figure 14:
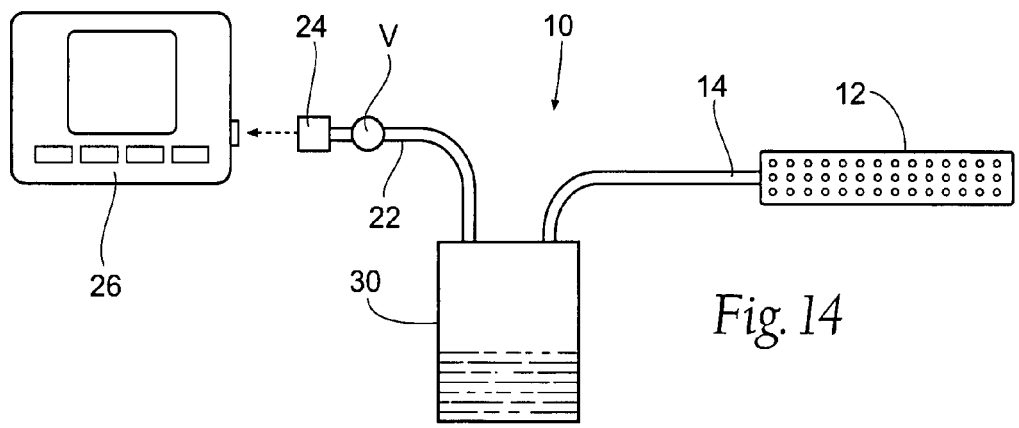
FIGS. 14 and 15 are representative views of various systems of a type shown in FIG. 4.
Figure 15:
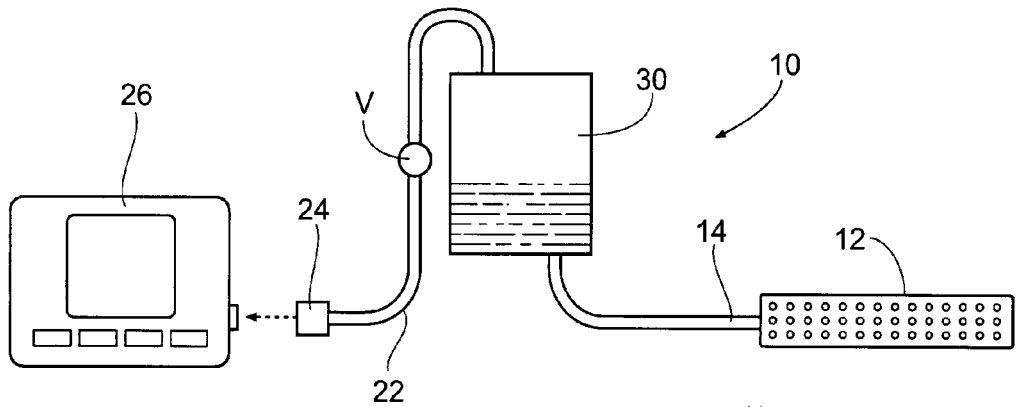

The wound drainage system 10 can be variously configured and assembled. For example, as shown in FIG. 14, the in-line reservoir 30 is intended, in use, to be placed at a gravity position at or below the drain assembly 12 and includes separate fluid inlet and vacuum outlet paths arranged along the top of the reservoir 20, coupled, respectively, to the internal drain assembly 12 and the external negative pressure suction device 26. As FIG. 15 shows, the reservoir 30 is intended, in use, to be placed at a gravity position above the drain assembly 12 and includes an fluid inlet path arranged along the bottom of the reservoir 30 (coupled to the drain assembly 12) and a vacuum outlet port arranged along the top of the reservoir 30 (coupled to the external negative pressure suction device 26).

Figure 18:
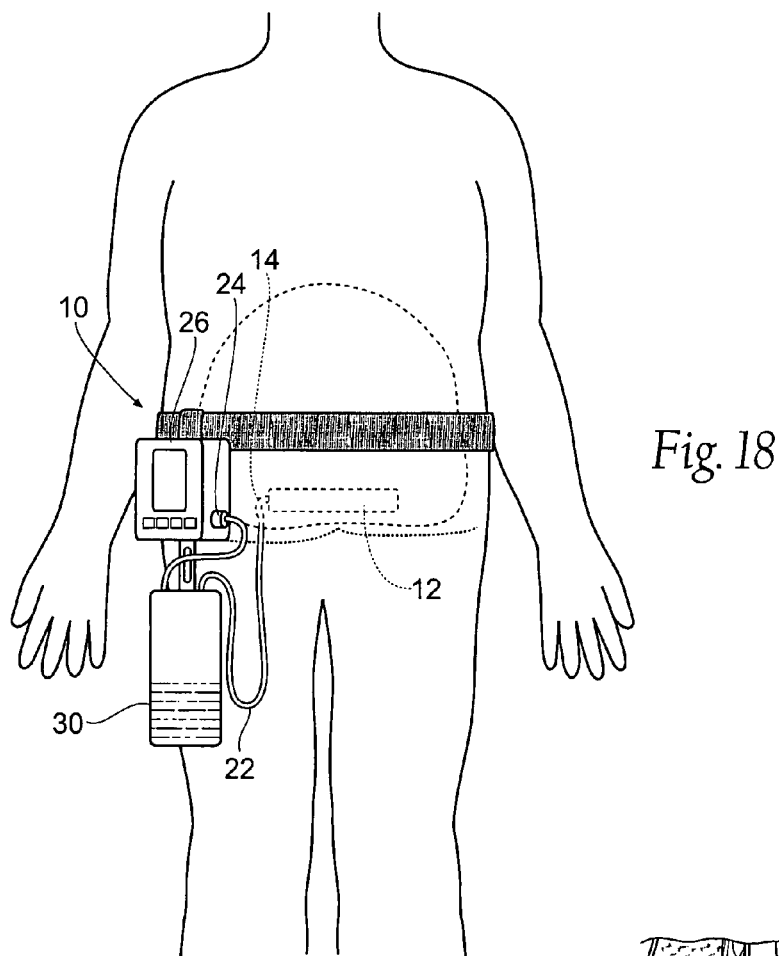
FIG. 18 shows, in an anatomic view, a system like that shown in FIG. 4, comprising a wound drain assembly coupled to a portable source of negative pressure that can be carried by an individual, but also be fixed or attached to a wall section.

As FIG. 18, the system 10 may include a battery powered external negative pressure suction device 26' that can be carried by the individual. The system 10 can therefore be operated while the individual ambulates, so that the individual need not be bed-bound during the recovery period.

Figure 19A:
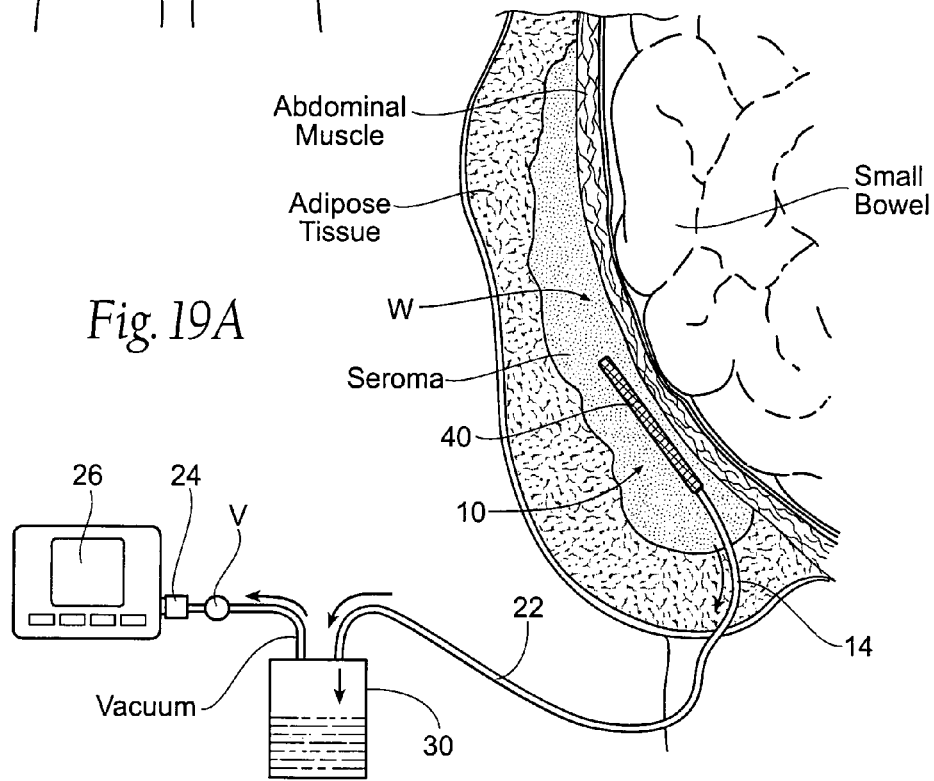

As shown in FIG. 19A, the internal drain assembly 12 can comprise an absorbable mesh structure 40 coupled to the tubing 12. The absorbable mesh structure 40 can be made of sterile material, such as, e.g., Vicryl, moncryl, PDS or other absorbable material that could be woven into a foam-like construct. In this embodiment, when the internal drain assembly 12 has completed its job (see FIG. 19B), the silicone or plastic tubing 14 is detached from mesh structure 40 and removed, leaving the absorbable mesh structure 40 inside the body, to dissolve and absorb just like absorbable suture, as shown in FIG. 19C.

It is believed that applying a vacuum of significant pressure internally and directly in a wound area or body cavity removes chronic edema and leads to increased localized blood flow. It is also believed that the applied forces applied internally and directly in a wound area result in the enhanced formation of tissue adherence. It is further believed that applying a vacuum of significant pressure internally and directly in a wound area or body cavity will accelerate healing by the application of a universal negative force to the entire wound volume, drawing the wound edges together, assisting closure, enhancing wound healing, and decreasing dead space and seroma. Presumed mechanisms responsible for achieving these objectives include: (i) changes in microvascular blood flow dynamic; (ii) changes in interstital fluid; (iii) removal of wound exudates; (iv) stimulation of growth factors and collagen formation; (iv) reduction in bacterial colonization; (v) mechanical closure of wound by "reverse tissue expansion;" (vi) increasing adherence of the soft tissue and internal wound healing; and (vii) decreasing dead space and seroma formation.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

We claim:

1. A method comprising creating percutaneous access into a wound defined by an interior dead space having a volume enclosed between interior tissue surfaces consisting of muscle, connective, or skin tissue containing blood vessels that have been separated by surgery or trauma within a body beneath substantially intact skin, and in which extracellular blood and serous fluid escaping from the blood vessels can accumulate to form a seroma, providing a wound drain assembly comprising a wound drainage structure sized and configured for placement entirely within the interior dead space, the wound drainage structure comprising a material capable of being absorbed by the body and being sized and configured to absorb extracellular blood and serous fluid in the interior dead space on substantially all sides of the material, and tubing releasably coupled to the wound drainage structure being sized and configured to be coupled to a source of negative pressure outside the body to convey negative pressure into the wound drainage structure for application internally throughout the interior dead space, placing the wound drainage structure entirely within the interior dead space, extending the tubing from the interior dead space through the percutaneous access to a location outside the body, coupling the tubing to a source of negative pressure outside the body, operating the source of negative pressure to convey negative pressure into the wound drainage structure for application internally throughout the interior dead space, in response to the applied negative pressure, conveying extracellular blood and serous fluid absorbed by the material from the interior dead space to decrease the volume of the dead space and subsequent seroma formation, in response to the applied negative pressure, drawing together the separated interior tissue surfaces to promote adherence of the tissue surfaces and a normal wound healing process, removing the tubing from the wound drain structure, and allowing the wound drainage structure to be absorbed by the body.

2. A method comprising creating percutaneous access into a wound defined by an interior dead space having a volume enclosed between interior tissue surfaces consisting of muscle, connective, or skin tissue containing blood vessels that have been separated by surgery or trauma within a body beneath substantially intact skin, and in which extracellular blood and serous fluid escaping from the blood vessels can accumulate to form a seroma, providing a wound drain assembly comprising a housing comprising an inert, non-tissue adherent material, the housing enclosing an open interior, the housing being sized and configured for placement entirely within the interior dead space, perforations in the housing communicating with the open interior sized to pass extracellular blood and serous fluid accumulated in the seroma, the perforations substantially surrounding all sides of the open interior to convey extracellular blood and serous fluid into the open interior, a foam sponge material comprising an open-cell porous structure or a granulated foam construction carried within the open interior to absorb extracellular blood and serous fluid conveyed through the perforations into the open interior, and tubing coupled to the open interior and extending from the interior dead space through the percutaneous access to a location outside the body, the tubing being sized and configured to be coupled to a source of negative pressure outside the body to convey negative pressure into the open interior of the housing for application through the perforations internally throughout the interior dead space, placing the housing entirely within the interior dead space, extending the tubing from the interior dead space through the percutaneous access to a location outside the body, coupling the tubing to a source of negative pressure outside the body, operating the source of negative pressure to convey negative pressure into the open interior of the housing for application through the perforations internally throughout the interior dead space, in response to the applied negative pressure, conveying extracellular blood and serous fluid absorbed by the foam sponge material from the interior dead space to decrease the volume of the dead space and subsequent seroma formation, and in response to the applied negative pressure, drawing together the separated interior tissue surfaces to promote adherence of the tissue surfaces and a normal wound healing process.

3. A method according to claim 2 wherein operating the source of negative pressure includes conveying negative pressure at 125 to 200 mmHg below ambient pressure into the open interior of the housing for application through the perforations internally throughout the interior dead space.

4. A method according to claim 1 wherein operating the source of negative pressure includes conveying negative pressure at 125 to 200 mmHg below ambient pressure into the open interior of the housing for application through the perforations internally throughout the interior dead space.

* * * * *